(12) United States Patent
Bocklet

(10) Patent No.: US 9,821,104 B2
(45) Date of Patent: Nov. 21, 2017

(54) EXTRACORPOREAL BLOOD TREATMENT DEVICE FOR OPERATION WITH A SINGLE PATIENT CONNECTION AND METHOD FOR OPERATION OF AN EXTRACORPOREAL BLOOD TREATMENT DEVICE WITH A SINGLE PATIENT CONNECTION

(71) Applicant: Fresenius Medical Care Deutschland GmbH, Bad Homburg v.d.H (DE)

(72) Inventor: Christoph Bocklet, Bad Bocklet (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 969 days.

(21) Appl. No.: 14/167,117

(22) Filed: Jan. 29, 2014

(65) Prior Publication Data

US 2014/0213957 A1 Jul. 31, 2014
US 2017/0252499 A2 Sep. 7, 2017

Related U.S. Application Data

(60) Provisional application No. 61/757,773, filed on Jan. 29, 2013.

(30) Foreign Application Priority Data

Jan. 29, 2013 (DE) .................. 10 2013 001 437

(51) Int. Cl.
*A61M 37/00* (2006.01)
*A61M 1/30* (2006.01)

(52) U.S. Cl.
CPC .............. *A61M 1/306* (2014.02); *A61M 1/30* (2013.01); *A61M 1/303* (2014.02); *A61M 2202/0413* (2013.01)

(58) Field of Classification Search
CPC .......... A61M 1/306; A61M 1/303; A61M 1/30
See application file for complete search history.

(56) References Cited

U.S. PATENT DOCUMENTS 4,231,366 A * 11/1980 Schael .................. A61M 1/30
128/DIG. 13
2010/0179467 A1* 7/2010 Gunther .............. A61M 1/3639
604/6.15

(Continued)

FOREIGN PATENT DOCUMENTS

DE 2 236 433 A 2/1974
DE 10 2008 050367 A1 4/2010
(Continued)

OTHER PUBLICATIONS

International Preliminary Report on Patentability from PCT/EP2014/050928, dated Aug. 4, 2015.

*Primary Examiner* — Tatyana Zalukaeva
*Assistant Examiner* — Ariana Zimbouski
(74) *Attorney, Agent, or Firm* — Kilyk & Bowersox, P.L.L.C.

(57) ABSTRACT

An extracorporeal blood treatment device for operation with a single patient connection, connected by an arterial and a venous blood line to an extracorporeal blood circuit, and a method for operating a blood treatment device with a single patient connection. The blood treatment device has two apparatuses for conveying blood in the arterial and venous blood lines. The second apparatus for conveying blood comprises means for collecting blood and means for establishing a pressure in the means for collecting blood, so that blood collected in the means for collecting blood flows to the patient connection. Furthermore, the blood treatment device has arterial and venous closure elements for interrupting the flow of liquid in the arterial and venous blood lines, as well as a control unit for actuating the two apparatuses for (Continued)

conveying blood and the arterial and venous closure elements. The blood treatment device and the method for operating are characterized in that the first apparatus for conveying blood is operated both during the arterial and venous phases, so that blood flows continuously through the blood treatment unit.

20 Claims, 2 Drawing Sheets

(56) References Cited

U.S. PATENT DOCUMENTS

2012/0029409 A1* 2/2012 Rada ................. A61M 1/30
 604/6.09
2014/0165733 A1* 6/2014 Jansson ................. A61M 1/30
 73/714

FOREIGN PATENT DOCUMENTS

| EP | 0 498 741 A1 | 12/1992 |
| EP | 2 415 491 A1 | 2/2012 |
| EP | 2 465 553 A1 | 6/2012 |
| WO | 2008/148506 A2 | 12/2008 |
| WO | 2010/037520 A1 | 4/2010 |

* cited by examiner

EXTRACORPOREAL BLOOD TREATMENT DEVICE FOR OPERATION WITH A SINGLE PATIENT CONNECTION AND METHOD FOR OPERATION OF AN EXTRACORPOREAL BLOOD TREATMENT DEVICE WITH A SINGLE PATIENT CONNECTION

CROSS REFERENCE TO RELATED APPLICATION

The present application claims priority to Application No. DE 10 2013 001 437.9, filed in the Federal Republic of Germany on Jan. 29, 2013, and U.S. Provisional Patent Application Ser. No. 61/757,773, filed on Jan. 29, 2013, each of which is expressly incorporated herein in its entirety by reference thereto.

FIELD OF INVENTION

The present invention relates to an extracorporeal blood treatment device for operation with a single patient connection, which is connected to an arterial and a venous blood line of an extracorporeal blood circuit. The present invention further relates to a method for operating an extracorporeal blood treatment device with a single patient connection.

BACKGROUND INFORMATION

Blood treatment devices with a blood treatment unit, through which blood from a patient flows, are generally known. For example, these include the known haemodialysis, haemofiltration or haemodiafiltration devices. Blood treatment devices can be operated with separate arterial and venous patient connections or with a single patient connection.

When operating a blood treatment device with a single patient connection, blood is removed and returned by means of a single cannula, to which both the arterial and venous blood lines are connected. The blood received from the patient during an arterial phase is stored in a reservoir and is supplied to the patient again from the reservoir in a venous phase.

An extracorporeal blood treatment device is known from WO 2008/148506 A2 in which the blood is conveyed into the blood treatment unit in the arterial phase and is conveyed from the blood treatment unit to a blood collecting vessel, wherein the blood supplied to the patient is interrupted. A predetermined pressure is built up in the blood collecting vessel, which is monitored. Due to the pressure, the blood collected in the blood collecting vessel is displaced from the blood collecting vessel in the venous phase and is supplied to the patient, while the blood supply to the blood treatment unit is interrupted, so that blood does not flow through the blood treatment unit during the venous phase.

When blood does not flow through the dialyser of a dialysis device continuously, there is a risk that the membrane of the dialyser becomes blocked (clotting). Blood treatment devices for single needle operation are known, in which blood flows through the dialyser continuously.

The problem of blockage of the dialyser membrane during the single needle dialysis is addressed in DE 42 17 692 A1, wherein a valve arrangement is proposed for control of fluid flow. In a preliminary step, blood is pumped from the patient by a blood pump via the dialyser into a buffer vessel and, in a following step, is pumped in the same direction of flow from the buffer vessel via the dialyser to the patient again. Between the two steps, the blood circulates by the dialyser in a closed circuit, from which the patient is separated by the valve arrangement, however, so that blood flow through the dialyser is not interrupted.

An extracorporeal blood treatment device for single needle operation with an extracorporeal blood circuit is known from WO 2010/037520 A1, which comprises two occluding pumps, which are positioned in the arterial blood line upstream and downstream of a blood collecting means. Both blood pumps are operated in the arterial and venous phases at different delivery rates. In the arterial phase, a higher delivery rate is set for the blood pump upstream of the blood collecting means than for the blood pump downstream of the collecting means, so that blood is withdrawn from the patient. In the venous phase, however, the delivery rate of the pump upstream of the blood collecting means is lower than the feed rate downstream of the collecting means, so that blood is supplied to the patient. The known device is intended to allow relatively small blood flow rates to be set. A disadvantage is that transmembrane flow over the dialyser membrane is possible.

DE 2 236 433 describes a dialysis device for single needle operation with an extracorporeal blood circuit, in which the blood pump, which is positioned in the arterial blood line upstream of the dialyser, is operated during the arterial and venous phases, so that blood is continuously conveyed through the dialyser. The dialysis device provides an arterial blood reservoir and a pressure chamber. In the arterial phase, the arterial tube clamp in the arterial blood line is open, while the venous tube clamp in the venous blood line is closed, so that blood is pumped from the patient into the pressure chamber. When the pressure in the chamber has reached a predetermined value, in the venous phase the venous tube clamp is opened and the arterial tube clamp is closed, so that blood is supplied from the pressure chamber to the patient. The substantial variations in pressure and pressure peaks occurring upstream of the dialyser have proved to be a disadvantage, since they can lead to an undesired and uncontrolled exchange of blood plasma over the membrane of the dialyser, wherein there is a risk of blocking of the dialyser membrane.

SUMMARY

An object of the present invention is to provide an extracorporeal blood treatment device that allows operation with a single patient connection without substantial pressure variations and pressure peaks. A further object of the present invention is a method for operating an extracorporeal blood treatment device with a single patient connection while avoiding the occurrence of substantial pressure variations and pressure peaks.

A further object of the present invention is to provide an extracorporeal blood treatment device for a single needle treatment, in which the risk of the formation of blood clots in the extracorporeal blood circuit is further reduced.

In turn, a further object of the present invention is to provide an extracorporeal blood treatment device for a single needle treatment, in which the required amount of anticoagulant agent, for example, heparin, is reduced.

In turn, a further object of the present invention is to provide an extracorporeal blood treatment device for a single needle treatment, in which clearance of the treated blood is further improved.

In turn, a further object of the present invention is to provide an extracorporeal blood treatment device for a single needle treatment, in which a haemodiafiltration operation is possible with addition of replacement fluid put 'online' before the dialyser and/or after the dialyser during the arterial phase and during the venous phase.

The blood treatment device in accordance with the present invention comprises two apparatuses for conveying blood in the arterial and venous blood line. The first apparatus for conveying blood can vary, while the second apparatus for conveying blood has means for collecting blood and means for establishing a pressure in the means for collecting blood, so that blood collected in the means for collecting blood flows to the patient connection. The blood treatment device further comprises an arterial and a venous closure element for interrupting the flow of fluid in the arterial or venous blood line, as well as a control unit for actuating the two apparatuses for conveying blood and the arterial and venous closure elements.

The blood treatment device in accordance with the invention and the method in accordance with the invention are characterized in that the first apparatus for conveying blood during both the arterial and the venous phases is operated so that blood flows through the blood treatment unit continuously. In the arterial phase, blood is conveyed at a predetermined first flow rate from the patient connection via the blood treatment unit to the means for collecting blood with the first apparatus, wherein the fluid flow is interrupted in the venous blood line to the patient connection. The arterial phase is followed by the venous phase, in which blood is conveyed at a predetermined second flow rate via the blood treatment unit into the means for collecting blood with the first apparatus.

In the arterial and venous phases, blood flows via the blood treatment unit at the first or second flow rate, wherein a specific volume of blood is removed from the patient in the arterial phase. This volume of blood is returned to the patient in the venous phase with the second apparatus for conveying blood. Pressure is established for this purpose in the means for collecting blood, so that blood flows at a predetermined third flow rate, which is greater than the first and second flow rates, from the means for collecting blood to the patient connection. At the patient connection, the blood flow divides into circulation flow and return flow. The establishment of a pressure in the means for collecting blood is necessary for conveying blood. It is unimportant for regulation whether a specific flow rate is predetermined with the means for establishing a pressure, so that a corresponding return pressure is set, or a specific return pressure is set, so that a corresponding flow rate is set. The volume of blood supplied in the venous phase to the patient is independent of the flow rate at which the blood flows through the closed circuit, which comprises the arterial and venous blood line and the blood treatment unit. Consequently, the first apparatus for conveying blood in the arterial and venous phases can be operated at the same or at different throughput rates. The third flow rate follows from the total of the volume flow of blood that is conveyed by the first apparatus and the volume flow of blood that is displaced from the means for collecting blood due to the return pressure.

The pressure in the extracorporeal blood circuit, in particular in the blood treatment unit, can be kept constant during the arterial and venous phases. In the venous phase, a return pressure can be set at a constant blood flow rate, while in the arterial phase this return pressure can be set with the means for establishing the pressure. Undesirable pressure fluctuations and pressure peaks can be avoided thereby. The blood flows in the venous and arterial phases can be freely set independent of one another. Furthermore, the circulation flow can be set independent of venous and arterial flows.

The first and second flow rate at which the blood is conveyed during the arterial and venous phases from the patient connection via the blood treatment unit to the means for collecting blood can be the same or can differ. Consequently, the first flow rate can be greater or smaller than the second flow rate. In practice, however, both flow rates will be substantially the same. The flow rate in the arterial phase can be slightly smaller than that in the venous phase, to avoid the arterial needle being drawn into the wall of the fistula or the patient shunt, due to the negative pressure on the suction side of the blood pump.

For the blood treatment device in accordance with the present invention and the method in accordance with the present invention, it is important that, during the venous phase, blood flows at a greater flow rate to the patient connection and at a lower flow rate from the patient connection, so that blood is supplied to the patient. In the arterial phase, blood only flows from the patient connection into the means for collecting blood, since the blood supply to the patient connection is interrupted.

For the present invention, it is unimportant where the arterial and venous blood lines are joined to the patient connection. In practice, the length of the segment of line between the junction of arterial and venous lines and the patient are kept as short as possible, however, because the volume of this segment of line is filled with already dialysed blood after the venous phase, so that this volume disadvantageously decreases the total stroke volume and reduces the efficiency of the treatment.

In a preferred embodiment of the present invention, the single patient connection is configured as a cannula with a distal and a proximal end, wherein a connection piece joining the arterial and venous blood lines is provided at the proximal end of the cannula. However, it is also possible for the connection piece for the blood lines not to be part of the patient connection.

The first apparatus for conveying blood can be configured in different ways. Preferably, the first apparatus for conveying blood is an occluding blood pump.

A particularly preferred embodiment of the present invention provides that this second apparatus for conveying blood has means for storing air, which comprises a closed volume, wherein the means for establishing a pressure and the means for storing air and the means for collecting blood have a flow connection, such that air can be transferred from the means for storage of air during displacement of the blood collected in the means for collecting blood into the means for collecting blood. In this embodiment, a closed volume is created that includes the means for storage of air and the means for collecting blood, together with the associated connecting lines. In principle, no air can penetrate into or leave this closed volume.

The means for compressing air can be configured in different ways; for example, a compressor can be provided for compressing air.

A further, particularly preferred embodiment provides that the second apparatus for conveying blood comprises a bypass line connecting the means for storing air and means for collecting blood, wherein a bypass valve is arranged in the bypass line. In the arterial phase, the bypass valve is opened, so that air is conveyed from the means for collecting blood into the means for storing air, while in the venous phase, the bypass valve is closed, so that, with the means for establishing a pressure, the air in the means for storing air is transferred into the means for collecting blood, so that the blood is displaced from the means for collecting blood. The bypass valve can be cycled in the arterial phase by means of a pressure regulator.

In the blood treatment device in accordance with the present invention, the control unit is configured so that all necessary components are actuated so that the individual process steps are carried out. The control unit can be a separate unit or a component of the central control unit of the extracorporeal blood treatment device. For example, the control unit can comprise a microprocessor, on which a data-processing program (software) runs.

The method in accordance with the present invention and the device in accordance with the present invention allow the setting of larger blood flows via the blood treatment unit than the blood flow with which blood is returned to the patient, wherein an improved clearance is obtained. Further, longer cycle times are possible, since the blood does not come to a stop. Due to the smaller risk of blocking of the membrane of the dialyser (clotting), it is possible to administer smaller amounts of heparin.

In the method according to the present invention and the device according to the present invention, the venous closure element is closed during the arterial phase. Thus, undesired recirculation is securely prevented.

An exemplary embodiment of the present invention is explained in detail in the following with reference to the drawings.

DETAILED DESCRIPTION

Figure 1:
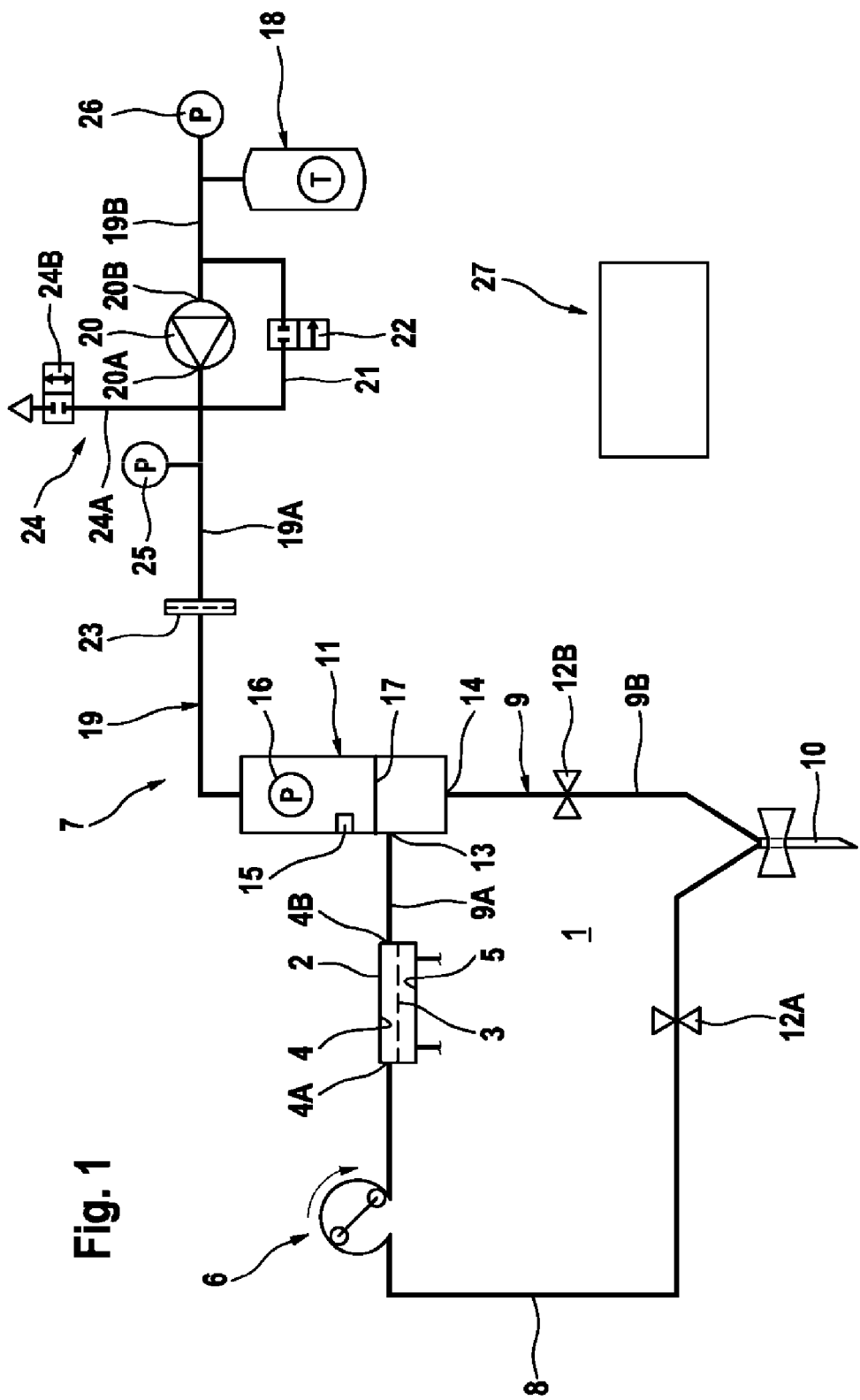
FIG. 1 shows the components of the extracorporeal blood treatment device for single needle operation in accordance with the present invention in a much simplified schematic representation.

FIG. 1 shows the components of the blood treatment device for single needle operation, in particular a dialysis device, in a much simplified schematic representation. The individual components of the blood treatment device are described in detail in WO 2008/148506 A2, which is incorporated herein in its entirety by reference thereto.

The blood treatment device comprises an extracorporeal blood circuit 1 with a blood treatment unit 2, for example, a dialysis machine. The dialysis machine 2 is subdivided by a semipermeable membrane 3 into a blood chamber 4 and a dialysis fluid chamber 5. The blood of the patient is conveyed in the extracorporeal blood circuit 1 by means of a first apparatus 6 for conveying blood and a second apparatus 7 for conveying blood. The first apparatus 6 for conveying blood is preferably an occluding tube pump. The dialysis fluid circuit is not shown in FIG. 1.

Figure 2:
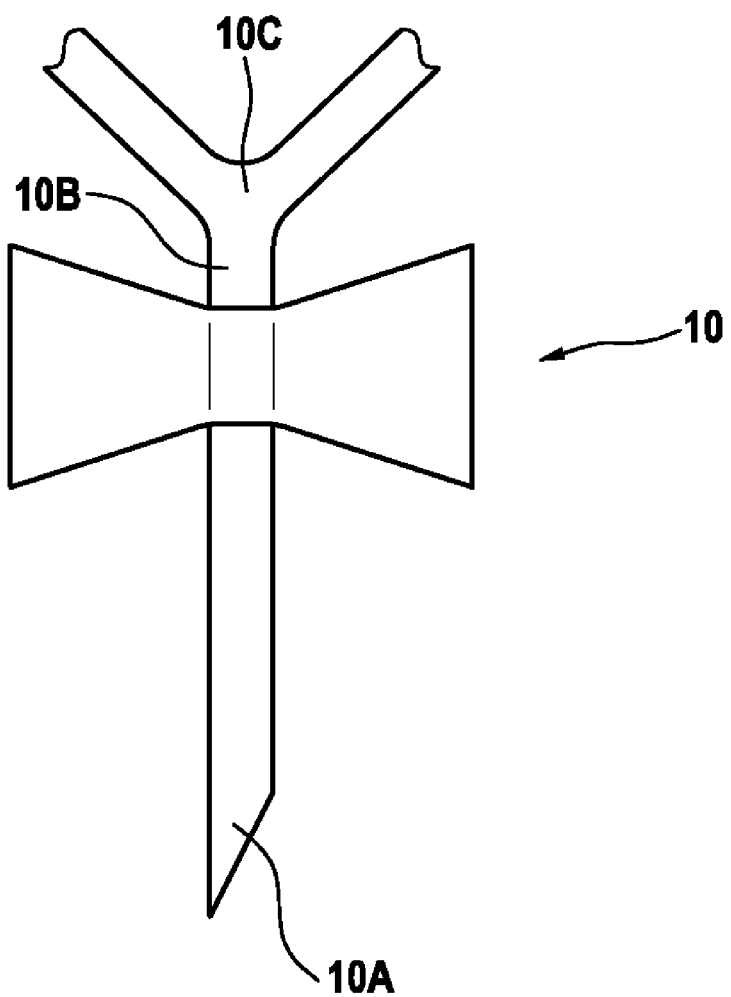
FIG. 2 shows the element 10 of FIG. 1 in enlarged representation.

A tube set is inserted in the blood treatment device and is discarded after the treatment. The tube set comprises an arterial blood supply line 8, which is inserted in the occluding tube pump 6, leading to the inlet 4A of the blood chamber 4 of the dialysis machine 2, and a venous blood return line leading from the outlet 4B of the blood chamber 4. Blood supply line and blood return line 8, 9 are attached to a common patient connection 10. The patient connection 10 is a cannula with a distal and a proximal end 10A, 10B. The proximal end 10B of the cannula 10 is configured as a connection piece 10C, to which the blood supply and return lines 8, 9 are attached (FIG. 2).

The second apparatus 7 for conveying blood comprises means 11 for collecting blood in which the blood return line 9 is positioned. The means 11 for collecting blood are configured as a vessel with a predetermined, closed volume. In the following, the means for collecting blood are described as blood collecting vessel 11.

Upstream of the blood pump 6 is an arterial closure element 12A in the blood supply line 8 for interrupting the blood supply line 8 and, downstream of the blood collecting vessel 11, a venous closure element 12B is positioned in the blood return line 9 for interrupting the blood return line. The closure elements 12A, 12B can be, for example, electromagnetically or pneumatically actuated tube clamps.

The blood collecting vessel 11 has an inlet 13, to which a first segment 9A of the blood return line 9 leads, and has an outlet 14, from which a second segment 9B of the blood return line 9 leaves. The level sensor 15 is provided to detect a specific filling level in the blood collecting vessel 11, to detect when the filling level in the blood collecting vessel has reached a predetermined value. Further, a pressure sensor 16 is provided to measure the pressure in the blood collecting vessel 11.

When the blood collecting vessel 11 is filled with blood, a certain volume of air remains above the liquid level 17 in the blood collecting vessel. The blood collecting vessel 11 has a flow connection with means 18 for storing gas, in particular air, which is configured as a vessel with a closed volume. In the following, the means 18 for storing gas is described as air reservoir.

So that the blood collecting vessel 11 and the air reservoir 18 can communicate with each other, a line 19 proceeds from the top of the blood collecting vessel, leading to the air reservoir 18. Means 20 for establishing a pressure in the blood collection chamber 11, which can be configured as a conventional compressor, for example, are positioned in the line 19. As long as the compressor 20 is not operated, the compressor interrupts the flow connection between the blood collecting vessel 11 and the air reservoir 18. During operation of the compressor 20, however, air in the air reservoir 18 is transferred into the blood collecting vessel 11. Since the air is compressed, a predetermined pressure is built up in the blood collecting vessel 11. The pressure is kept substantially constant by means of the regulated compressor 20.

The line 19 comprises two line segments 19A, 19B, of which the one line segment 19A connects the blood collecting vessel 11 to the pressure-side connection 20A of the compressor 20 and the other line segment 19B connects the suction-side connection 20B of the compressor 20 to the air reservoir 18. These line segments 19A, 19B form a connecting line 19 for transferring air from the air reservoir to the blood collecting vessel.

A bypass line 21 is provided to allow transfer of air from the blood collecting vessel 11 to the air reservoir 18 when the compressor 20 is not in operation, proceeding from the first line segment 19A of the line 19 and leading to the second line segment 19B of the line 19. A bypass valve 22 is connected into the bypass line 21. Together with the corresponding line segments of the line 19, the bypass line 21 forms a connecting line for conveying air from the blood collecting vessel 11 to the air reservoir 18.

In order to prevent fluid from passing out of the blood collecting vessel 11 into the air reservoir 18, a filter 23 is positioned in the first line segment 19A of the line 19, containing a hydrophobic, impermeable membrane, i.e., permeable to air, but impermeable to liquid.

To supply air to and remove air from the closed volume, which comprises the blood collecting vessel 11 and the air reservoir 18, together with the line 19, means 24 are provided for supplying and removing air, which comprises an air supply/removal line 24A connected to the first line segment 19A of the line 19 with an air supply/removal valve 24B.

Apart from the pressure sensor 16 for measuring the pressure in the blood collecting vessel 11, a pressure sensor 25 is provided for measuring the pressure in the first line segment 19A of the line 19 between the filter 23 and the compressor 20, and a further pressure sensor 26 is provided for measuring the pressure in the air reservoir 18.

The blood treatment device can have in addition a substituate supply for a pre- or post-dilution from a substituate source (not shown) via a substituate line (not shown), which can be attached to the arterial blood line 8 upstream of the blood treatment unit 2 or the venous blood line 9 downstream of the blood treatment unit 2.

The blood treatment device has a central control unit 27, which is connected by electrical lines (not shown) to the blood pump 6, the arterial and venous tube clamps 12A, 12B, the bypass valve 22, the air supply/removal valve 24B, the level sensor 15, the compressor 20, and the pressure sensors 16, 25 and 26.

The operation of the dialysis device is described in detail in the following. The central control unit 27 controls the individual components of the blood treatment device as follows.

The pressure in the blood collecting vessel 11 is referred to in the following as chamber pressure and the pressure in the air reservoir 18 as reservoir pressure.

At the start of the actual dialysis treatment, the system is initialized, as described in WO 2008/148506 A2. During the operation of the blood treatment device, the control unit 27 successively switches between an arterial and a venous phase, wherein the blood pump 6 is operated in both the arterial and the venous phases.

At the start of the arterial phase, the control unit 27 opens the arterial closure element 12A and closes the venous closure element 12B. The blood pump 6 is operated in the arterial phase at a predetermined delivery rate, so that blood is conveyed in the blood supply line 8 from the patient connection 10 at a predetermined flow rate $Q_{(1)a}$ into the blood collecting vessel 11. The volume of blood conveyed by the blood pump 6 is removed directly from the patient. For example, the blood pump conveys blood at a flow rate of 300 ml/min. Consequently, the blood collecting vessel 11 is filled with blood. While this is proceeding, an undesired recirculation cannot occur, since the venous closure element 12B is closed. The compressor 20 stops in the arterial phase.

The bypass valve 22 is opened by the control unit 27 in the arterial phase, so that the air displaced from the blood collecting vessel 11 passes via the bypass line 21 into the air reservoir 18. Consequently, the reservoir pressure rises. The bypass valve 22 is particularly preferred to be a digital valve that is unregulated in the open state. Such a digital valve is particularly cost-effective. The digital valve is operated in a cyclic manner, to keep pressure fluctuations small. Cycling of the opening period of the valve can particularly preferably take place at a frequency of 1 Hz to 6 Hz. Alternatively, it is also possible to use a proportional valve, though this incurs higher costs.

As soon as the mass of air contained in the blood collecting vessel 11 and the line volume has reached a predetermined amount, which is calculated from the desired stroke volume and the desired return pressure, the control unit 27 closes the bypass valve 22. As a result, two separate volumes of air are formed, i.e., the volume of air in the blood collecting vessel 11 with the associated line segments and the volume of the air reservoir 18 with the associated line segments.

In the venous phase, the arterial closure element 12A is opened and the bypass valve 22 is closed. The control unit 27 opens the venous closure element 12B in the venous phase. The blood pump 6 is operated in the venous phase at a delivery rate $Q_{(1)v}$, which can be the same as the delivery rate of the blood pump in the arterial phase $Q_{(1)v}=Q_{(1)a}$, for example 300 ml/min. However, the delivery rate of the blood pump 6 in the venous phase can also be greater or smaller than the delivery rate in the arterial phase.

The compressor 20 is operated at the venous phase and conveys air from the air reservoir 18 into the blood collecting vessel 11, in order to establish a pressure, so that blood is conveyed from the blood collecting vessel. In doing so, the compressor 20 is operated so that the desired return pressure is produced in the blood collecting vessel 11. Specification of a return pressure defines a corresponding blood flow rate. The return pressure is specified so that the set blood flow rate corresponds to the target value. Thus, the return pressure is regulated in order to set the corresponding flow rate. Since the air is continuously supplied to the blood collecting vessel 11 from the air reservoir 18, the reservoir pressure continuously decreases.

Due to the simultaneous operation of the blood pump 6 and the compressor 20 in the venous phase, a blood flow rate is produced in the blood return line 9 downstream of the blood collecting vessel 11, resulting from the total of the volume of blood $Q_{(1)v}$ conveyed by the blood pump 6 and the volume of blood $Q_{(2)v}$ displaced from the blood collecting vessel 11. Since the blood pump 6 is also operated during the venous phase, the flows $Q_{(1)v}$ and $Q_{(2)v}$ split again at the patient connection 10. Thus, it is solely the rate at which the level drops in the blood collecting container 11 that determined the venous return flow $Q_{(2)v}$ into the patient. This return flow $Q_{(2)v}$ is independent of the circulation flow $Q_{(1)v}$, which is set in the closed circuit, which comprises the arterial and venous blood lines 8, 9 and the blood chamber 4 of the dialyser 2. Due to the continuous operation of the blood pump 6 in the venous and arterial phases, blood flows continuously through the blood chamber 4 of the dialyser 2. Dialysis fluid always flows continuously through the dialysis fluid chamber 5.

In the present exemplary embodiment, the compressor 20 is operated so that the return pressure required for setting the desired blood flow is established. At the same time, the compressor 20 is so regulated that the return pressure is essentially constant, thus resulting in an essentially constant blood flow.

An alternative exemplary embodiment of the present invention does not provide regulation of the return pressure, but regulates the volume flow in the blood collecting vessel 11 so that the corresponding return pressure is set in the blood collecting vessel 11. In an alternative exemplary embodiment, analogous to a level measurement, the pressure is measured in the blood collecting vessel 11 with the pressure sensor 16 at two points in time. The measurement of pressure, in each case at two points in time, can be made continuously over the whole period of treatment. The variation of the volume of blood in the blood collecting vessel 11 can be calculated from the two pressure measurements for the two points in time from the change of volume per unit time of the volume flow rate. This calculation can be carried out continuously during the treatment. The speed of the compressor 20 is regulated, so that the calculated volume flow rate corresponds to the predetermined target flow rate. The return pressure is thus adjusted in this exemplary embodiment on the basis of compressor speed.

What is claimed is:

1. An extracorporeal blood treatment device for operation with a single patient connection, which is connected to an arterial blood line and a venous blood line of an extracorporeal blood circuit, the extracorporeal blood circuit further comprising a dialyzer having a blood chamber that is in fluid communication with the arterial blood line and the venous blood line, the blood treatment device comprising:
   a blood pump;
   a apparatus pressurized air system for conveying blood and comprising a vessel for collecting blood that flows through the venous blood line from a blood treatment unit, and an air compressor for establishing a pressure in the vessel for collecting blood, such that blood collected in the vessel for collecting blood flows to the single patient connection;
   an arterial closure element for interrupting the flow of liquid in the arterial blood line;
   a venous closure element for interrupting the flow of liquid in the venous blood line; and
   a control unit for actuating the blood pump and the pressurized air system for conveying blood, and for actuating the arterial and venous closure elements, the control unit comprising a software program and a microprocessor on which the software program runs;
   wherein the control unit is configured to actuate the blood pump, the air compressor for establishing a pressure in the vessel for collecting blood, the arterial closure element, and the venous closure element such that
      in an arterial phase, the blood pump is operated with an open arterial closure element and a closed venous closure element, at a predetermined first delivery rate, such that blood flows at a predetermined first flow rate ($Q_{(1)a}$) from the single patient connection via the blood treatment unit into the vessel for collecting blood,
      in a venous phase following the arterial phase, the blood pump is operated with an open arterial closure element and an open venous closure element at a predetermined second delivery rate, such that blood flows at a predetermined second flow rate ($Q_{(1)v}$) from the single patient connection via the blood treatment unit into the vessel for collecting blood,
      in the venous phase, a pressure is established in the vessel for collecting blood with the air compressor for establishing a pressure in the vessel for collecting blood, such that blood flows at a predetermined third flow rate from the vessel for collecting blood to the single patient connection; and
      the blood pump is continuously operated in both the arterial phase and the venous phase such that blood flows continuously through the blood chamber of the dialyzer;
   wherein there is continuous switching between the arterial phase and the venous phase.

2. The blood treatment device according to claim 1, wherein the predetermined first flow rate ($Q_{(1)a}$) is equal to the predetermined second flow rate ($Q_{(1)v}$).

3. The blood treatment device according to claim 1, wherein the predetermined first flow rate ($Q_{(1)a}$) is greater than or less than the predetermined second flow rate ($Q_{(1)v}$).

4. The blood treatment device according to claim 1, wherein the single patient connection is configured as a cannula with a distal end and a proximal end, wherein a connection piece connecting the arterial blood line and the venous blood line is provided at the proximal end of the cannula.

5. The blood treatment device according to claim 2, wherein the single patient connection is configured as a cannula with a distal end and a proximal end, wherein a connection piece connecting the arterial blood line and the venous blood line is provided at the proximal end of the cannula.

6. The blood treatment device according to claim 1, wherein the blood pump is configured as an occluding blood pump.

7. The blood treatment device according to claim 4, wherein the blood pump is configured as an occluding blood pump.

8. The blood treatment device according to claim 1, wherein the pressurized air system for conveying blood further comprises an air reservoir for storing air, which comprises a closed volume, wherein the air compressor for establishing a pressure is in flow connection with the air reservoir for storing air and the vessel for collecting blood, such that air can be transferred from the air reservoir for storing air into the vessel for collecting blood while displacing the blood collected in the vessel for collecting blood.

9. The blood treatment device according to claim 4, wherein the pressurized air system for conveying blood further comprises an air reservoir for storing air, which comprises a closed volume, wherein the air compressor for establishing a pressure are in flow connection with the air reservoir for storing air and the vessel for collecting blood, such that air can be transferred from the air reservoir for storing air into the vessel for collecting blood while displacing the blood collected in the vessel for collecting blood.

10. The blood treatment device according to claim 8, wherein the pressurized air system for conveying blood further comprises a bypass line connecting the air reservoir for storing air and the vessel for collecting blood, and a bypass valve positioned in the bypass line.

11. The blood treatment device according to claim 9, wherein the pressurized air system for conveying blood further comprises a bypass line connecting the air reservoir for storing air and the vessel for collecting blood, and a bypass valve positioned in the bypass line.

12. A method for operating an extracorporeal blood treatment device with a single patient connection, which is connected to an arterial blood line and a venous blood line of an extracorporeal blood circuit, the extracorporeal blood circuit further comprising a dialyzer having a blood chamber that is in fluid communication with the arterial blood line and the venous blood line, the method comprising the following steps:
   in an arterial phase, conveying blood at a predetermined first flow rate ($Q_{(1)a}$) from the single patient connection via a blood treatment unit into a vessel for collecting blood, wherein the flow of liquid to the patient connection is interrupted;
   in a venous phase following the arterial phase, conveying blood at a predetermined second flow rate ($Q_{(1)v}$) from the single patient connection via the blood treatment unit into the vessel for collecting blood; and
   establishing a pressure in the vessel for collecting blood, such that blood flows at a predetermined third flow rate from the vessel for collecting blood to the single patient connection; and continuously operating a blood pump on the arterial blood line during both the arterial phase and the venous phase such that blood flows continuously through the blood chamber of the dialyzer;

wherein there is continuous switching between the arterial phase and the venous phase.

13. The method according to claim 12, wherein the predetermined first flow rate ($Q_{(1)a}$) is equal to the predetermined second flow rate ($Q_{(1)v}$).

14. The method according to claim 12, wherein the predetermined first flow rate ($Q_{(1)a}$) is greater than or less than the predetermined second flow rate ($Q_{(1)v}$).

15. The method according to claim 12, wherein the blood is conveyed by an occluding blood pump from the single patient connection via the blood treatment unit into the vessel for collecting blood.

16. The method according to claim 13, wherein the blood is conveyed by an occluding blood pump from the single patient connection via the blood treatment unit into the vessel for collecting blood.

17. The method according to claim 14, wherein the blood is conveyed by an occluding blood pump from the single patient connection via the blood treatment unit into the vessel for collecting blood.

18. The method according to claim 12, wherein, while establishing a pressure in the vessel for collecting blood, air is transferred from an air reservoir for storing air into the vessel for collecting blood, while displacing blood collected in the vessel for collecting blood.

19. The method according to claim 13, wherein, while establishing a pressure in the vessel for collecting blood, air is transferred from an air reservoir for storing air into the vessel for collecting blood, while displacing blood collected in the vessel for collecting blood.

20. The method according to claim 15, wherein, while establishing a pressure in the vessel for collecting blood, air is transferred from an air reservoir for storing air into the vessel for collecting blood, while displacing blood collected in the vessel for collecting blood.

* * * * *

UNITED STATES PATENT AND TRADEMARK OFFICE
CERTIFICATE OF CORRECTION

PATENT NO. : 9,821,104 B2
APPLICATION NO. : 14/167117
DATED : November 21, 2017
INVENTOR(S) : Christoph Bocklet It is certified that error appears in the above-identified patent and that said Letters Patent is hereby corrected as shown below:

In Claim 1, at Column 9, Line 14, please delete the word "apparatus."

In Claim 12, at Column 10, Line 63, please delete the word "and."

Signed and Sealed this
Tenth Day of April, 2018

Andrei Iancu
*Director of the United States Patent and Trademark Office*